United States Patent [19]

Welker

[11] 4,403,518
[45] Sep. 13, 1983

[54] SAMPLER APPARATUS

[75] Inventor: Robert H. Welker, Sugar Land, Tex.

[73] Assignee: Welker Engineering Company, Sugar Land, Tex.

[21] Appl. No.: 251,134

[22] Filed: Apr. 6, 1981

[51] Int. Cl.³ .............................................. G01N 1/14
[52] U.S. Cl. .................................. 73/864.34; 417/479
[58] Field of Search ........................ 73/863.84, 864.34; 92/89, 90; 417/401, 479, 480, 99

[56] References Cited

U.S. PATENT DOCUMENTS

| 2,267,280 | 12/1941 | Kuhnel | 417/480 |
| 2,711,134 | 6/1955 | Hughes | 417/497 |
| 3,945,770 | 3/1976 | Welker | 417/401 |

FOREIGN PATENT DOCUMENTS 334922 9/1930 United Kingdom ................ 417/479

OTHER PUBLICATIONS

Inline Relief and Sampler Head Assemblies, A 9 page brochure by Welker Engineering Co., P.O. Box 1228, Bellaire, TX 77401.

Primary Examiner—S. Clement Swisher
Attorney, Agent, or Firm—Gunn, Lee & Jackson

[57] ABSTRACT

An improved sampler is enclosed. In the preferred and illustrated embodiment, the sampler comprises a compressable sample collection head formed of a resilient material having a dished area therein which head is pushed by a push rod against a mating or facing surface of harder material. The collection head is encased in a shield. The improved apparatus includes a projecting mounting post extending into the collection head and which is bonded thereto, further including an undercut portion having an enlarged overhanging shoulder to secure the collection head. This prevents separation of the collection head from the push rod.

8 Claims, 2 Drawing Figures

FIG.1
FIG.2
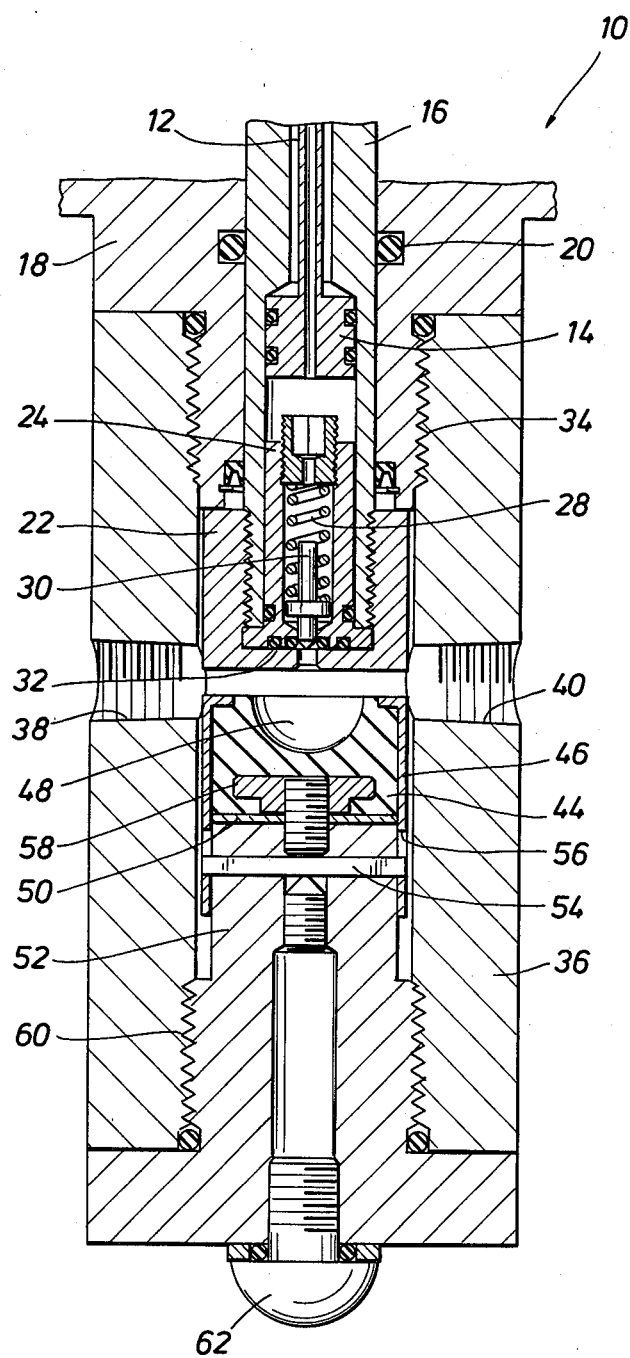
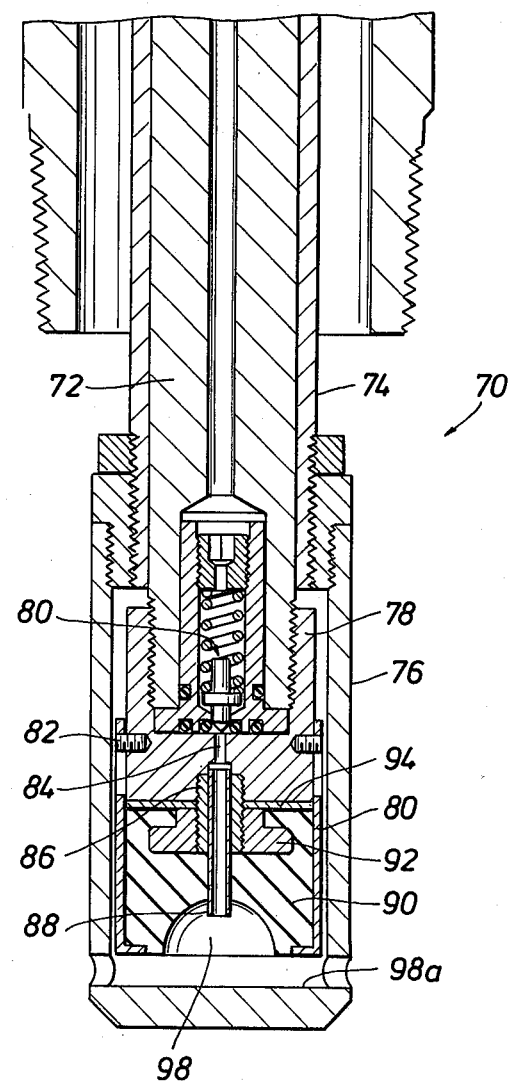

SAMPLER APPARATUS

BACKGROUND OF THE DISCLOSURE

As disclosed in U.S. Pat. No. 3,945,770 of the present inventor, sample collection apparatus utilizing a collection head has been devised. The sample collection apparatus is particularly valuable in obtaining a small sample for analytical purposes. Sometimes, it is very difficult to get a small sample out of a large flow. This difficulty finds analogy in attempting to draw a thimble full of water from a fire hydrant. When it is turned on, it is almost impossible to get only a thimble full. The apparatus of the referenced patent provides a means whereby small samples can be obtained from any size flow in a pipeline or other vessel.

This is equipment which is intended to be installed and left indefinitely to operate for months without significant service. The present disclosure is directed to improvements in that apparatus. These improvements particularly assist in extending the life of the equipment. In larger diameter sample collection heads which must be used to collect larger samples, there is real risk of material fatigue in the collection head which destroys the effectiveness of the equipment after prolonged operation. The life of the equipment is thereby limited, depending on the rate of operation and other scale factors. As has been discovered in the perfecting of the disclosed apparatus, there is a tendency for the sample collection head to form a high vacuum as it works against an opposing face formed of non yielding material. The formation of vacuum on the exposed face of the sample collection head forms tensile stress in the collection head. This tensile stress eventually will strain the collection head and perhaps permanently damage it. This deformation can take several forms. In one form, the deformation is first found at the bond between the push rod and the sample collection head. This bond typically will tear or break. The resilient plug tears along a line determined by the overhanging lip locking over the end of the plug. This situs of failure is geometrically determined.

The present apparatus is an improvement which incorporates a means securing the collection head. Thus, when the push rod forces the collection head against the opposing face, the dished area disappears as the collection head resiliently yields against this force. A natural restoring force in this resilient material is created as the push rod is retracted. In light of the fact that the sample collection head is not normally bonded to a washer and is captured slidably within a surrounding cylindrical shield, an internal restoring force normally does restore the collection head to its intended and original shape. However, the stress and consequential bond rupture which occurs as described above will interfere with this operation after continued use depending on a number of scale factors. The scale factors involved include the type of rubber, the dimensions of the collection head, the depth of the indention formed in the head, and many other factors. It is sufficient to note that the apparatus disclosed herein markedly improves the performance of the sample collection head. Accordingly, this apparatus is an improved sample gathering apparatus wherein the improvement incorporates a projecting mounting post which extends into the body of the resilient material which forms the collection head. The resilient material is shaped into a plug and has a dished exposed face. The mounting post is undercut to define a grasping shoulder where, at the time of fabrication, the plug is held on the push rod.

BRIEF DESCRIPTION OF THE DRAWINGS

So that the manner in which the above-recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be notd, however, that the appended drawings illustrate only typical embodiments of the invention and are not to be considered limiting of its scope, for the invention may admit to other equally effective embodiments.

FIG. 1 is a sectional view through a first embodiment of the present apparatus disclosing the improved sample collection head of the present invention within sample collection apparatus; and FIG. 2 discloses an alternate embodiment of the present invention wherein the sample collection head incorporates a shoulder equipped mounting post having the collection head bonded thereto.

DETAILED DESCRIPTION OF THE PREFERRED AND ILLUSTRATED EMBODIMENTS

Attention is first directed to FIG. 1 of the drawings. FIG. 1 discloses an apparatus which is found in sample collection equipment. Briefly, the structure 10 in FIG. 1 incorporates a centrally mounted tubing 12 which reciprocates in response to a motive means (not shown). The tubing 12 has an enlargement 14 which aligns the tubing 12. The tubing 12 is a pilot line for removal of the sample which is obtained by the apparatus. The surrounding shaft 16 is received within a fixed cylindrical body 18 and passes through a seal 20 comprising an O-ring. The shaft 16 and tubing 12 move in unison. The push rod 16 terminates in a set of threads and receives a cylindrical cap around it. The cap 22 closes over the end of the push rod 16. The push rod 16 is axially hollow to receive the tubing 12. In addition, space is provided in it to introduce a sample into the tubing 12 through a check valve mechanism.

The check valve mechanism includes a body 24, the body 24 being received substantially within the push rod 16. It is closed at the upper end by a plug 26 which is threaded into it. The plug 26 is hollow. The plug 26 has an axial passage through it to enable the sample to flow from the check valve. The plug 26 closes over the inner body 24. A coil spring 28 is received within the liner and bears against a check valve element 30. The check valve element 30 has a shoulder for receiving the spring 28 around it. Moreover, the valve element 30 has a tapered or chamfered face which seats against a cooperating valve seat machined in the inner body 24 at the lower centered portion thereof. The inner body 24 thus has a central opening to function as a valve seat. It is undercut to have room for additional seals at 32. The seals 32 prevent leakage into the cap 22 which is threaded around the lower end of the push rod. The cap 22 has an aligned central opening.

As will be understood in FIG. 1, a check valve mechanism defines a path of flow past the valve element 30 into the tubing 12. The fluid pressure must overcome the bias spring 28. Moreover, the pressure required to operate is high in the preferred embodiment.

The surrounding fixed cylindrical body 18 has an external set of threads at 34 which enable a cylindrical body to be placed thereabout, the body bearing the numeral 36. The body 36 is threaded to the threads 34. It includes an inlet opening 38 and an outlet opening 40. These openings are drilled into the axial passage and are aligned adjacent the upper most location of the push rod 12. In order words, through suitable plumbing connected at the fittings 38 and 40, fluid flow is introduced into the apparatus immediately adjacent to the cap 22.

The push rod 16 is in the upper position. Its range of travel is limited by the abutement of the upper end of the cap 22 at the threaded skirt having the threads 34 thereon.

The cap 22 is positioned in space opposite to a collection head 44. The collection head 44 is received within a surrounding shield 46. The shield has an overhanging lip which secures the collection head within the shield. The collection head is comprised of a resilient material formed into a cylindrical plug. It has a dished area at 48. This indention receives fluid in the relaxed state and captures it by sealing against the opposing face. In this instance, the opposing face is a part of the cap 22. Moreover, the resilient material which defines the collection head is captured within the shield 46. It is able to telescope within the shield by sliding upwardly and downwardly within a limited range of movement. The resilient material which comprises the cylindrical plug is mounted adjacent to a washer 50, and is bonded to the washer 50. It serves as a backing member. The washer 50 is abutted against a cylindrical solid body 52. The cylindrical body 52 fits snuggly within the shield 46. Telescoping movement is permitted within limits. Telescoping movement requires that the shield 46 slide over the cylindrical body 52. Rotation is prevented by means of a pin 54 which extends through slots 56 in the shield 46. The compression of the head 44 is accompanied by telescoping movement of the shield 46 downwardly as viewed in FIG. 1.

The present apparatus includes an upstanding mounting post 58. The post 58 is undercut so as to have an overhanging shoulder. The plug of resilient material is cast about the post 58. This enables it to bond to the post and to particularly bond on all sides surrounding the overhang. Moreover, the overhang grips the resilient body which is cast about it and pulls when the occasion requires expansion of the collection head.

The cylindrical body 52 is received within the surrounding cylindrical body 36 and is joined to it by means of threads 60. Moreover, a long bolt 62 is threaded through an axial opening in the cylindrical body 52 and the bolt is sufficiently long to thread into the post 58. This joins the post 58 mechanically to the cylindrical body 52 and thereby fixes it in location. Intersection of the guide pin 54 with the bolt 62 must be accommodated and one suitable technique for this is to utilize two separate bolts or to incorporate an elongate slot or window within the bolt 62 to permit the pin 54 to pass through it. The pin 54 is captured in position and cannot escape after it has been installed as shown in FIG. 1.

In operation, the push rod 16 is forced downwardly to drive the cap 22 against the sample collection head 44. When it contacts against it, the resilient material 44 forms a seal around the cavity or chamber 48. This captures the fluid of interest which is introduced through the inlet passage to the equipment. As the push rod moves further, the cavity 48 is reduced in volume, thereby increasing the pressure on the captured fluid. This pressure increases until it exceeds the opposing pressure of the spring 28, and flows pass the valve element 30. By contrast, the check valve closes after the chamber is reduced to its minimum size. As the chamber expands, the check valve 30 moves against the seat and prevents leakage back into the chamber. This forms a partial vacuum as the push rod moves away, thereby permitting the cavity 48 to restore its original shape. As this shape is obtained, the vacuum which is created within the cavity adheres the sample collection head 44 to the facing cap. The cap functions somewhat in the fashion of a hammer working against an anvil, applying a force to the plug 44 for the purposes described. On release, there is a tendency for the resilient plug 44 to adhere by vacuum force to the cap. This pulls it out of the shield 46. While the shield will grip it to an extent, permanent extrusion having the form of a distortion may occur. As this happens, the resilient plug 44 pulls or tears along a stress line in the plug after cumulative fatigue. The present invention contemplates placing the post having an undercut shoulder within the plug to secure the plug of resilient material whereby tears of the bonded material are prevents. Even should the bonding break free, the undercut defining the resilient plug which fully surrounds the post prevents detachment of the plug from the opposite face. This prevents the plug from adhering to the cap 22 and being fulled from the shield 46.

As will be observed in the foregoing, the sample collection head is a fixed part of the equipment and the push rod works against it. The movement is relative, namely, the working face of the collection head 44 is held stationary while the push rod forces the cooperative face against it. This arrangement enables the check valve and outlet line to be positioned in the push rod, and further permits the resilient plug to be installed with reasonable access to service the resilient plug, as for instance, by replacing it.

FIG. 2 shows an embodiment identified by the numeral 70 which reverses the position of the sample collection head. Accordingly, FIG. 2 includes the telescoped and movable push rod 72 received within a fix sleeve 74. The fixed sleeve in turn is joined to a surrounding cylindrical housing 76 which housing is hollow. In the up position of the push rod 72, an anvil 78 moves with the push rod 72. The anvil 78 is concentrically received within the shield 80. The shield 80 telescopes and its range of movement is limited by set screws 82. The set screws 82 are received within suitable lengthwise slots which permits telescoping movement of the shield on the exterior of the anvil. Moreover, the push rod 72 terminates at a check valve fitting 80 which is constructed similarly to the check valve previously described. It differs in that the anvil closes over the lower end of the check valve assembly 80 and includes an internal passage 84. The passage 84 through the anvil is directed toward an attachment screw 86. The screw 86 supports a collection tubing 88 which extends into the sample head 90. The attachment screw 86 further includes the undercut mounting post 92. The mounting post 92 is adjacent to a backing washer 94 which is captured by the attachment screw 86. The screw 86 thus aligns the collection tube 88 and threadly joins the sample head 90 to the anvil. The cavity 96 is positioned opposite a working face 98 which is internally constructed within the hollow cylindrical housing 76 previously mentioned. Suitable ports introduce the fluid of interest for collection as a sample.

This equipment positions the sample collection head 90 on the end of the push rod. In other words, the sample collection head reciprocates with the push rod and works against the face 98 which is relatively stationary. As will be understood in contrasting FIGS. 1 and 2, the push rod is arranged differently relative to the sample collection head and the two embodiments.

From the foregoing, the embodiment 70 operates in the same fashion. One difference is that the compressed fluid recovered in the sampling equipment exits through the tubing 88. This tubing is cut short so that it does not jam against the opposite working face on compression of the resilient plug 90. The sample which is recovered flows through the tubing 88 and past the check valve assembly 80. It is then recovered in the same manner as the equipment shown in FIG.

Again, there is a tendency for the collection head to be eventually damaged by a vacuum pull on the return stroke. The mounting post 92 shown in FIG. 2 secures this resilient plug in a manner to prevent this kind of damage. Moreover, the undercut shoulder enables a firm grip to be maintained whereby the bond, plus the shape of the parts, secures the two together and extends the life of the apparatus.

While the foregoing is directed to the preferred embodiment of the present invention, other and further embodiments of the invention may be devised without departing from the basic concept thereof is determined by the claims which follow.

I claim:

1. In a sampler having a resilient cylindrical plug, a shield surrounding said plug and defining an end exposed face of the plug having an indention formed therein and which end exposed face is opposite a cooperative facing plate, and wherein the indention of the exposed face is subjected to contraction in response to movement of a push rod relatively moving said plug towards said facing plate to seal there against and capture a fluid in the indention thereof, the apparatus further including a rigid pump support body, a rigid restraining washer being positioned in contact with said rigid pump support body and forming an aperture, said resilient cylindrical plug being in intimate contact with said restraining washer, a projecting mounting post secured to said rigid pump body and extending through said aperture of said washer and into said plug from an end thereof opposite said indention wherein said mounting post includes an undercut portion with an enlarged overhang shoulder and wherein said shield overhangs the exposed face of said plug and cooperates with said mounting post to hold said plug within said shield.

2. The apparatus of claim 1 wherein said post is concentric, circular in shape, and has a fully encircling and overhanging shoulder adjacent to the undercut portion.

3. The apparatus of claim 1 or 2 wherein said mounting post is connected to the end portion of said push rod.

4. The apparatus of claim 1 wherein said mounting post is within said resilient plug which is cast thereabout.

5. The apparatus of claim 4 wherein said pump support body is hollow and has a flow tube positioned therein.

6. The apparatus of claim 4 wherein said pump support body is hollow and is internally threaded axial passage therein to receive a mounting bolt.

7. the apparatus of claim 1 wherein said shield is slidably positioned for movement axially in a specified range of movement along said plug.

8. The apparatus of claim 1 wherein said plug is attached to said rigid restraining washer so that plug retention is cooperatively maintained by said projecting mounting post, said shield and said rigid restraining washer.

* * * * *